United States Patent [19]

Dockner et al.

[11] 4,156,784
[45] May 29, 1979

[54] MANUFACTURE OF CARBAMATES

[75] Inventors: Toni Dockner, Meckenheim; Harro Petersen, Frankenthal, both of Fed. Rep. of Germany

[73] Assignee: BASF Aktiengesellschaft, Fed. Rep. of Germany

[21] Appl. No.: 831,750

[22] Filed: Sep. 9, 1977

Related U.S. Application Data

[63] Continuation of Ser. No. 638,954, Dec. 8, 1975, abandoned.

[30] Foreign Application Priority Data

Dec. 18, 1974 [DE] Fed. Rep. of Germany ....... 2459765

[51] Int. Cl.$^2$ ............................................ C07C 125/04
[52] U.S. Cl. ..................................... 560/157; 560/132; 560/162; 560/163; 560/164; 560/165; 560/166
[58] Field of Search ............... 560/157, 166, 132, 162, 560/163, 164, 165

[56] References Cited

U.S. PATENT DOCUMENTS

| | | | |
|---|---|---|---|
| 2,834,799 | 5/1958 | Sowa | 260/482 C |
| 3,013,065 | 12/1961 | Beinfest | 260/482 C |
| 3,873,553 | 3/1975 | Hearsey | 260/482 C |

FOREIGN PATENT DOCUMENTS 1643635 7/1971 Fed. Rep. of Germany ....... 260/482 C

OTHER PUBLICATIONS

Kirk–Oihmer, "Encyclopedia of Chemical Technology," pp. 871–899, (1967), vol. 11.
Nacod, "Ion Exchange Technology," pp. 272–279, (1956).
Calmon, "Ion Exchange in Organic and Biochemistry," pp. 658–659, (1957).

*Primary Examiner*—James O. Thomas, Jr.
*Assistant Examiner*—Michael Shippen
*Attorney, Agent, or Firm*—Keil & Witherspoon

[57] ABSTRACT

Carbamates are manufactured by reaction of alcohols with urea in the presence of ion exchangers containing nickel.

The products are starting materials for the manufacture of textile finishing agents, dyes and plant protection agents.

8 Claims, No Drawings

MANUFACTURE OF CARBAMATES

This a continuation, of application Ser. No. 638,954 filed Dec. 8, 1975 now abandoned.

The present invention relates to a process for the manufacture of carbamates by reaction of alcohols with urea in the presence of ion exchangers containing nickel.

Houben-Weyl, Methoden der Organischen Chemie, volume 8, page 190 et seq. discloses that alcohols may be reacted with urea to give carbamates. The yields from the process are unsatisfactory, even using a fairly long reaction time and a large excess of alcohol, since by-products, eg. biuret, allophanic acid esters and cynauric acid, are produced. It is true that the yields can be improved by using zinc acetate, lead acetate or cobalt chloride (Z. Naturforsch., 1 (1946), 520) or using metal salts and metals, or which zinc dust, zinc oxide, vanadium pentoxide, tin(IV) chloride and tin(II) chloride, zinc salts, manganese acetate, chromium acetate, lead acetate, uranyl acetate, silver nitrate and copper sulfate have been given as examples (German Patent 752,127). However, the carbamates thus obtained still contain a certain proportion of the above by-products, which precludes their use in all syntheses which require starting materials of the highest purity. Thus, eg. such crude carbamates cannot be used directly for the manufacture of dimethylol compounds which are employed as finishing agents for chlorine-resistant finishing of textiles, and instead must first be purified by renewed distillation, or recrystallization.

If the method of the above German patent—which does not mention nickel salts—is followed, and the metal catalysts described are used, with glycol monoethers in place of monohydric alkanols as the starting materials, it is not only the purity of the end product but also, in many cases, its yield which is unsatisfactory. The Table which follows shows the results obtained in reacting urea with methylglycol (molar ratio 1:3) to give methoxyethylene-carbamate.

TABLE
(Reaction temperature 130° C. reaction time 25 hours)

| Catalyst | Amount of catalyst based on urea (% by weight) | Yield based on urea (% of theory) |
|---|---|---|
| Boron trifluoride | 1 | 50 |
| Aluminum acetate | 5 | 55 |
| Manganese sulfate | 5 | 57 |
| Sodium aluminate | 5 | 58 |
| Sodium tetrafluoborate | 1 | 63 |
| Copper filings | | 70 |
| Tin(IV) chloride | 5 | 85 |

Further, German Published Application 1,643,635 discloses the manufacture of hydroxyethylene-carbamate ethers by reaction of ethylene glycol monoethers with urea at from 100° to 150° C. in the presence of nickel compounds. It is true that the yields are 94% of theory, but, as shown by the Examples, reaction times of at least 21 hours are needed. Nickel compounds, in the said application, means nickel salts; nickel chloride is employed in the Examples.

It is an object of the present invention to provide a new process by means of which a large number of carbamates can be manufactured more simply and more economically, in better yield and purity and with a better space-time yield.

We have found that this object is achieved and carbamates of the formula

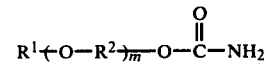

where $R^1$ is an aliphatic, cycloaliphatic or araliphatic radical which may be interrupted by one or more

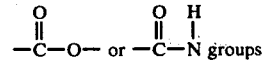

and/or oxygen atoms, $R^2$ is an aliphatic radical of at least 2 carbon atoms which is optionally interrupted by one or more

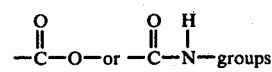

and/or oxygen atoms, or is

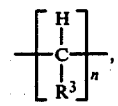

where the $R^3$'s may be identical or different and each is a cycloaliphatic, araliphatic or aromatic radical, and n is an integer from 2 to 6, and m is 0 or a positive integer, or $R^1$ is

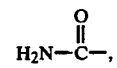

or phenyl or—if m is not less than 1—hydrogen, are obtained advantageously by a process wherein alcohols of the formula

    II where $R^1$, $R^2$ and m have the above meanings, are reacted with urea in the presence of ion exchangers containing nickel.

When using methylglycol, the reaction can be represented by the following equation:

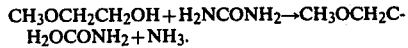

Compared to the conventional process, the process of the invention gives a large number of carbamates more simply and more economically, in better yield and purity and with better space-time yield. Compared to the process disclosed in German Published Application 1,643,635, the new process offers advantages in that the reaction time is substantially reduced and is in general from 5 to 10 hours and the space-time yield is increased by a factor of 3–4. In the light of the cited publications, it is surprising that the process of the invention gives a large number of carbamates by a simple method, in better yield and purity and without formation of by-products. The carbamates obtained by the new process conform to the highest standards of purity and can, e.g., be reacted, without prior purification, with formaldehyde to give the above dimethylol compounds used for chlorine-resistant textile finishes, thereby offering a labor-saving and more economical method of manufacture of assistants, eg. ordinary textile finishes and resin textile finishes. Particularly in view of German Published Application 1,643,635, it would have been expected that the new process would not give better yields and better purity and would even give poorer results, since—contrary to the teaching of the said published application, according to which only nickel salts should be used, in amounts of from 0.1 to 5% by weight based on urea—the proces of the invention is carried out with cation exchangers and the nickel bonded as a cation to the exchanger. After completion of the reaction, neither nickel nor dissolved nickel salts remain in the reaction mixture and such salts can thus, in the light of the process described in German Published Application 1,643,635, not react with the carbamate formed so as to induce a reverse reaction or the formation of undesirable by-products. The process according to the invention offers a further advantage that the ion exchangers containing nickel can be re-used as frequently as desired without regeneration.

The starting materials used are urea and alcohols of the formula II. Preferred starting materials II and, accordingly, preferred end products I, are those where $R^1$ is alkyl of 1 to 18, preferably of 1 to 10, and especially of 1 to 7, carbon atoms which may be interrupted by several, or in particularly by one,

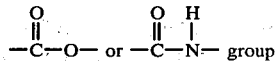

and/or by oxygen atoms, preferably by from 1 to 6 and especially 1 or 2 oxygen atoms, or $R^1$ is cycloalkyl of 5 or 6 carbon atoms or aralkyl of 7 to 12 carbon atoms, $R^2$ is alkylene of 2 to 18, preferably 2 to 10, and especially 2 to 7, carbon atoms which may be interrupted by several, or in particular by one,

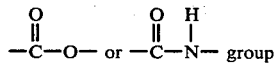

and/or by oxygen atoms, preferably by from 1 to 6 and especially 1 or 2 oxygen atoms or $R^2$ is alkylene of 4 to 18, preferably 4 to 10, and especially 4 to 7, carbon atoms which may be interrupted by several, or in particular by one,

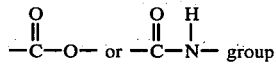

and/or by oxygen atoms, preferably from 1 to 6 and especially 1 or 2 oxygen atoms, and is advantageously the radical

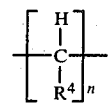

where the $R^4$'s may be identical or different and each is hydrogen or alkyl of 1 to 7 carbon atoms and n is an integer from 2 to 6, preferably 2, 3 or 4, or

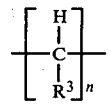

where the $R^3$'s may be identical or different and each is cycloalkyl of 5 or 6 carbon atoms or aralkyl of 7 to 12 carbon atoms or phenyl, and n is an integer from 2 to 6, preferably 2, 3 or 4, and m is 0 or an integer from 1 to 50, preferably from 1 to 28, and especially 0, 1, 2, 3, 9 or 18, or $R^1$ is, phenyl or—if m is not less than 1—hydrogen or

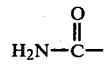

If m is greater than 1, several $R^2$'s, which may be identical or different, are present. The above radicals may further be substituted by groups which are inert under the reaction conditions, eg. alkyl or alkoxy each of 1 to 4 carbon atoms, carbamoyl, carbalkoxy of 2 to 6 carbon atoms, hydroxyl or carbamato.

The urea may be employed in the reaction in a stoichiometric amount or less, preferably in an amount of from 0.5 to 1 mole per mole of starting material II in the case of a free hydroxyl group. If 2 hydroxyl groups are present, the monocarbamate is suitably obtained if from 0.5 to 1 mole of urea is used per mole of starting material II, mixtures of monocarbamate and dicarbamate are obtained if larger amounts of urea, of up to 2 moles per mole of starting material II, are employed, and the dicarbamate alone is obtained if from 2 to 2.5, preferably from 2 to 2.2, moles of urea are employed per mole of starting material II. Analogously, in the case of polyhydroxy-alcohols, it is possible, by using stoichiometric or correspondingly reduced amounts of urea, to produce monocarbamates, dicarbamates, tricarbamates, tetracarbamates and polycarbamates in the pure form or as a mixture of carbamates, whereof the components depend on the molar ratio of the starting materials and the number of hydroxyl groups in the alcohol II. Thus, eg., depending on the molar ratio of urea, the alcohols shown below can give the following corresponding carbamates:

| Alcohol | Carbamate |
|---|---|
| HOCH$_2$CH$_2$CH$_2$OH | HOCH$_2$CH$_2$CH$_2$OCONH$_2$ and H$_2$NCOOCH$_2$CH$_2$CH$_2$OCONH$_2$ |
| HOCH$_2$CH$_2$CH$_2$CH$_2$OH | HOCH$_2$CH$_2$CH$_2$CH$_2$OCONH$_2$ and H$_2$NCOOCH$_2$CH$_2$CH$_2$CH$_2$OCONH$_2$ |
| HOCH$_2$CH=CH—CH$_2$OH | HOCH$_2$CH=CH—CH$_2$OCONH$_2$ and H$_2$NCOOCH$_2$CH=CHCH$_2$OCONH$_2$ |
| HOCH$_2$CH$_2$OCH$_2$CH$_2$OH | HOCH$_2$CH$_2$OCH$_2$CH$_2$OCONH$_2$ and H$_2$NCOOCH$_2$CH$_2$OCH$_2$CH$_2$OCONH$_2$ |
| HOCH$_2$—C(CH$_3$)$_2$—COOCH$_2$—C(CH$_3$)$_2$—CH$_2$OH | HOCH$_2$—C(CH$_3$)$_2$—COOCH$_2$—C(CH$_3$)$_2$—CH$_2$OCONH$_2$, |

-continued

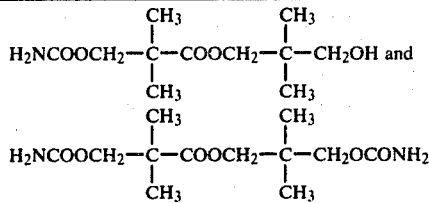

Preferred starting materials II are: C₄H₉OH, C₁₀H₂₁OH, C₁₇H₃₅OH,

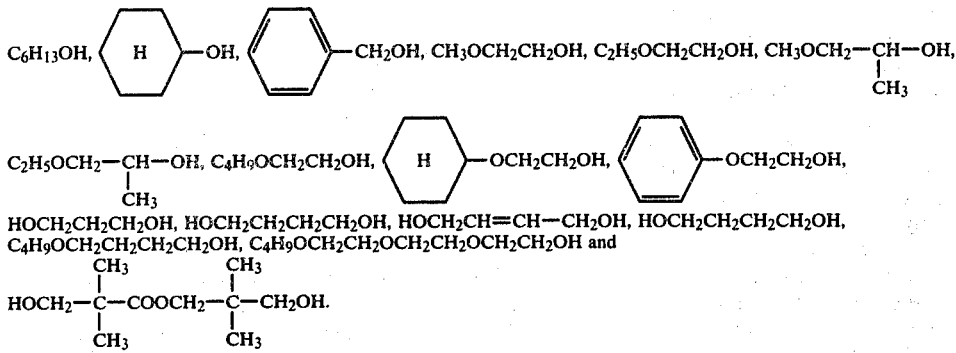

HOCH₂CH₂CH₂OH, HOCH₂CH₂CH₂CH₂OH, HOCH₂CH=CH—CH₂OH, HOCH₂CH₂CH₂CH₂OH,
C₄H₉OCH₂CH₂CH₂CH₂OH, C₄H₉OCH₂CH₂OCH₂CH₂OCH₂CH₂OH and $$\text{HOCH}_2-\underset{\underset{CH_3}{|}}{\overset{\overset{CH_3}{|}}{C}}-\text{COOCH}_2-\underset{\underset{CH_3}{|}}{\overset{\overset{CH_3}{|}}{C}}-\text{CH}_2\text{OH}.$$

However, it is also possible to use, eg. the following alcohols as starting materials II: 1,3,5-trihydroxypentane, 2-acetoxy-1-ethanol, 2-acetamido-1-ethanol, cyclopentyl alcohol, phenylethyl alcohol, decyl alcohol, octadecyl alcohols and the following alcohols, which are either unsubstituted or substituted, at the ω-hydroxyl group, by the radicals specified or the radicals described in connection with the above preferred individual alcohols II: hydroxypropyl-(1) alcohol, hydroxypropyl-(2) alcohol, hydroxyl-n-butyl-(1) alcohol, hydroxy-n-buten-(2,3)-yl-(1) alcohol, hydroxyethoxyethyl-(1) alcohol, triethylene glycol, hydroxy-pivalato-(3)-neopentyl-(1) alcohol, α-hydroxyacetylamido-(3)-neopentyl-(1) alcohol, ω-hydroxydecyl-(1) alcohol, ω-hydroxy-2,4,6-triethyl-octanyl-(1) alcohol, 2-hydroxy-2-cyclohexylethyl-(1) alcohol, 2-hydroxy-2-benzylethyl-(1) alcohol, 2-hydroxy-2-phenylethyl-(1) alcohol and 6-hydroxyethyl-(1) alcohol.

The reaction is as a rule carried out at from 100° to 160° C., preferably at from 125° to 150° C., under atmospheric or superatomspheric pressure, continuously or batchwise. In general, the starting material II also serves as the reaction medium though, if appropriate, organic solvents which are inert under the reaction conditions may be used, eg. aromatic hydrocarbons such as benzene, toluene, ethylbenzene, o-, m- and p-xylene, isopropylbenzene and corresponding mixtures. The amount of solvent used is suitably from 200 to 10,000% by weight, preferably from 200 to 1,000% by weight, based on starting material II. If the alcohol II alone is the reaction medium, an appropriate additional amount thereof is added to the starting mixture.

The reaction is carried out in the presence of ion exchangers—as a rule acid ion exchangers, and preferably acid synthetic ion exchange resins—which contain nickel. Such exchangers include all the cation exchangers described in Houben-Weyl, Methoden der Organischen Chemie, volume I/1, page 528, Table 3. Exchangers of strong to medium acidity, eg. phenolic resins or polystyrenesulfonic acid resins, or exchangers containing appropriate acid resins, eg. bifunctional condensation resins, are used preferentially. It is also possible to use polystyrenephosphonic acid resins, polystyrenephosphonic acid resins, resorcinol resins and aliphatic or aromatic carboxylic acid resins. The above cation exchangers are commercially available, eg. under the registered tradenames Amberlite, Lewatite, Lewasorb and Amberlyst, specific examples being Amberlyst 15, Amberlite 200, Lewatit CA 9259, Lewatit S 100 and Lewasorb V 100. Before the reaction, the exchangers are charged with nickel in accordance with conventional methods, suitably by a treatment with solutions, advantageously aqueous solutions, of nickel salts. Suitable nickel salts are nickel chloride, nickel acetate, nickel bromide, nickel nitrate and, preferably, nickel sulfate. The nickel compounds may also be in the form of corresponding hydrates, eg. nickel chloride hexahydrate. However, nickel phosphate, nickel carbonate, nickel bicarbonate, nickel borate, nickel oxalate and nickel propionate may also be used. Before treating the exchanger, the water which may be present in the exchanger can be removed by passing organic solvents, such as alcohols, eg. methanol, ethers, eg. glycol monoethers or tetrahydrofuran, or acetals, eg. of formaldehyde, through the exchanger. Preferably, the exchanger is activated, prior to the treatment with the nickel salt, by means of an acid, suitably sulfuric acid, hydrochloric acid or the acid corresponding to the anion of the nickel salt. The exchanger is advantageously first left for from 10 to 30 minutes under or in water at from 15° to 40° C. and is then activated for from 10 to 60 minutes with acid, suitable in the form of an aqueous solution of from 2 to 15 percent strength by weight, at from 15° to 40° C., after which the exchanger is washed with water until neutral.

The treatment with the nickel salt solution is suitably carried out at from 10° to 50° C., preferably from 20° to 30° C. It may be carried out under atmospheric or superatomspheric pressure, batchwise, eg. by a stirring-in or batch method, or, preferably, continuously, eg. in exchange columns, in a fixed bed, flowing bed or fluidized bed in tray columns. Suitably, nickel salt solutions of from 5 to 50 percent strength by weight are used, the treatment times being from 10 to 60 minutes. After the treatment, it is advantageous to rinse the exchanger with water until the wash liquor, or the wash liquor issuing from the exchange column, gives a neutral reaction, and then to wash the exchanger for from 10 to 60 minutes, at from 15° to 40° C., with one of the above inert solvents or an alcohol, in the case of liquid alcohols II preferably with the particular alcohol II which is to be used (for the reaction), until the exchanger is substantially free from water. Suitably, one part by weight of exchanger is charged with from 0.01 to 0.2, preferably from 0.02 to 0.1, and especially from 0.02 to 0.08, part by weight of nickel, and from 0.01 to 0.25, preferably from 0.02 to 0.1, part by weight of exchanger is then used per part by weight of urea.

The reaction may be carried out as follows: a mixture of urea, starting material II, exchanger and, where used, the solvent, is kept for from 7 to 12 hours at the reaction temperature. It is advantageous to remove the ammonia produced during the reaction from the reaction solution by passing nitrogen through the latter. The reaction mixture is then cooled and filtered. The end product is isolated from the filtrate by conventional methods, eg. by distillation. The uncovered starting material II and the ion exchanger, containing nickel, which has been filtered off, can be returned to the reaction.

The compounds which may be manufactured by the process of the invention are valuable starting materials for the manufacture of textile finishing agents, dyes and plant protection agents. For example, they can be methylolated to give textile finishing agents which give a good wrinkle-resist effect and finishing effect together with a softer, harder or fuller hand, depending on the structure of the finishing agent. Information on uses may be found in the publications cited earlier.

In the Examples which follow, parts are by weight.

EXAMPLE 1

(a) Manufacture of the nickel-containing catalyst

A column is filled with 1,000 parts of cation exchanger, which is allowed to stand in 1,000 parts of water for 15 minutes. 500 parts of 10 percent strength by weight hydrochloric acid are then added, the column is left to stand for 20 minutes and the cation exchanger is then washed neutral with distilled water. 3,400 parts of a 10 percent strength by weight solution of $NiSO_4 \cdot 7H_2O$ are then charged onto the activated exchanger. When the solution leaving the column no longer reacts acid, the uptake of nickel salt has ended. The exchanger charge is washed neutral with water and then washed free from water with dioxane or the fluid alcohols II to be used for the carbamate synthesis. The exchanger is now ready to use and contains 0.065 part of nickel per part of exchanger.

(b) Reaction

$CH_3OCH_2CH_2OCONH_2$

A mixture of 300 parts of urea, 684 parts of methylglycol and 18 parts of a cation exchanger which is commercially unavailable under the registered name Amberlite 200 and, having been treated in accordance with Example (1a), contains nickel, is heated, with stirring, to reflux temperature (130° C.) in the course of 20 minutes, in a stirred apparatus equipped with a reflux condenser. After reaching the reflux temperature, a slight stream of nitrogen bubbles is passed through the reaction mixture. The reflux temperatures rises to from 148° to 150° C. in the course of 5.5 hours, The reaction temperature is then kept at 149° C. After a total reaction time of 7 hours, the reaction solution is cooled to about 120° C. and the exchanger is filtered off.

Excess methylglycol is distilled off reduced pressure. 586 parts of methoxyethyl carbamate are obtained. This corresponds to a yield of 98.5% of theory, based on urea employed. On distilling the carbamate at a pressure of 0.1 mm Hg, a distillation residue of only 0.8% by weight is left. The carbamate has a boiling range of from 96° to 98° C. at 0.1 mm Hg.

EXAMPLE 2

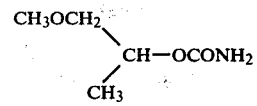

300 parts of urea, 810 parts of methoxyisopropanol and 18 parts of a cation exchanger which is commercially available under the registered name Amberlite 200 and, having been treated in accordance with Example (1a), contains nickel, are mixed in a stirred apparatus and the mixture is heated to the reflux temperature (125° C.) in the course of 30 minutes, whilst stirring. The mixture is then heated at the reflux temperature for 8 hours, whilst a stream of nitrogen is passed through it. The reflux temperature rises to 140° C. After the reaction solution has cooled, the exchanger is filtered off and excess methoxyisopropanol is distilled off under reduced pressure. 652 parts of methoxyisopropyl carbamate (98% of theory, based on urea) are obtained. The carbamate boils at 92° C. under 0.2 mm Hg and leaves a distillation residue of only 0.9% by weight.

Melting point=53°-54° C.

EXAMPLE 3

$C_2H_5OCH_2CH_2OCONH_2$ 300 parts of urea, 810 parts of ethylglycol and 15 parts of a cation exchanger which is commercially available under the registered name Amberlyst 15 and, having been treated in accordance with Example (1a), contains nickel, are heated to the reflux temperature (138° C.) in a stirred vessel. After 2 hours, the reflux temperature rises to 148° C. The reaction mixture is kept at this temperature for a further 8 hours, whilst a slight stream of nitrogen is passed through it. After filtering off the exchanger, excess ethylglycol is distilled off under reduced pressure. 645 parts of ethoxyethyl carbamate are obtained. This corresponds to 97% of theory, based on urea. On distilling the crude carbamate in a high vacuum, the end product distils at 110° C. under 0.2 mm Hg. A distillation residue of 0.9% is left.

EXAMPLE 4

$C_4H_9OCH_2CH_2OCONH_2$ 60 parts of urea are mixed with 177 parts of butylglycol and 3 parts of a cation exchanger which is commercially available under the registered name Lewatit CA 9259 and, having been treated in accordance with Example (1a), contains nickel, in a stirred apparatus. The mixture is heated to 135° C., whilst stirring. It is then heated for 10 hours at 140° C. After cooling, the mixture is filtered and the excess butylglycol is distilled from the filtrate under reduced pressure. 158 parts of n-butoxyethyl carbamate (corresponding to 98% of theory, based on urea) are obtained. On distillation of the end product in a high vacuum, a residue of only 0.9% by weight is left. The pure butoxyethyl carbamate has a boiling point 118°–120° C. at 0.2 mm Hg.

EXAMPLE 5

C₄H₉OCH₂CH₂OCH₂CH₂OCONH₂

600 parts of urea, 2,916 parts of butyldiglycol and 28 parts of a cation exchanger which is commercially available under the registered name Amberlite 200 and, having been treated in accordance with Example (1a), contains nickel, are heated for 10 hours at 150° C. in a stirred vessel, whilst a slight stream of nitrogen is passed through the mixture. The exchanger is then filtered off whilst the solution is still hot and the excess butyldiglycol is distilled off under reduced pressure. 1,988 parts of butyldiglycol carbamate are obtained. This corresponds to a yield of 97%, based on the amount of urea employed. The carbamate has a boiling range of 146°–148° C. at 0.2 mm Hg and leaves a distillation residue of 1.1% by weight.

EXAMPLE 6

C₄H₉OCH₂CH₂OCH₂CH₂OCH₂CH₂OCONH₂

A mixture of 120 parts of urea, 741 parts of butyltriglycol and 5 parts of a cation exchanger which is commercially available under the registered name Amberlite 200 and, having been treated in accordance with Example (1a), contains nickel, is heated for 10 hours at 145° C. in a stirred vessel whilst a slight stream of nitrogen is passed through the mixture. The exchanger is filtered off whilst the reaction solution is hot and the excess butyltriglycol is distilled off under reduced pressure. 493 parts of butyltriglycol carbamate are obtained. This corresponds to a yield of 99% of theory, based on urea. The carbamate has a boiling range of 172°–175° C. at from 0.2 to 0.3 mm Hg.

EXAMPLE 7

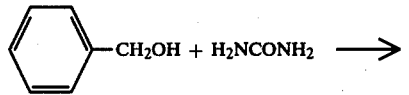

A mixture of 240 parts of urea, 778 parts of benzyl alcohol and 11 parts of a cation exchanger which is commercially available under the registered name Amberlyst 15 and, having been treated in accordance with Example (1a), contains nickel, is heated to the reflux temperature (131° C.) in a stirred vessel. In the course of 6 hours, the reflux temperature rises to 149° C. The reaction mixture is then heated at 149°–150° C. for a further 2 hours. After filtering off the exchanger, excess benzyl alcohol is removed by distillation under reduced pressure. 586 parts of benzyl carbamate are obtained. This corresponds to a yield of 97% of theory, based on urea. Benzyl carbamate boils at 116°–118° C. under from 0.3 to 0.4 mm Hg. Melting point=75°–76° C. On distillation, a residue of 1% by weight is left.

EXAMPLE 8

C₆H₁₃OCONH₂

A mixture of 918 parts of hexyl alcohol, 300 parts of urea and 14 parts of a cation exchanger which is commercially available under the registered name Amberlite 200 and, having been treated in accordance with Example (1a), contains nickel, is heated to 130° C. whilst stirring. The temperature is then raised to 150° C. in the course of 6 hours and maintained thereat for a further 4 hours. After filtering off the exchanger, excess hexyl alcohol is distilled off under reduced pressure. 680 parts of hexyl carbamate (94% of theory) are obtained. Melting point=56°–57° C.

EXAMPLE 9

HOCH₂CH₂CH₂OCONH₂

410 parts of 1,3-propanediol, 180 parts of urea and 11 parts of a cation exchanger which is commercially available under the registered name Amberlite 200 and, having been treated in accordance with Example (1a), contains nickel, are heated at 150° C. for 10 hours in a stirred apparatus, whilst a slight stream of nitrogen is passed through the mixture. The exchanger is then filtered off and excess propanediol is evaporated off under reduced pressure. On distillation in a high vacuum at 138°–140° C. and 0.1 mm Hg, 350 parts of γ-hydroxypropyl carbamate (98% of theory) are obtained. The distillation in a high vacuum leaves a residue of only 0.9% by weight.

EXAMPLE 10

C₁₇H₃₅OCONH₂

A mixture of 256 parts of heptadecyl alcohol, 60 parts of urea and 5 parts of a cation exchanger which is commercially available under the registered name Amberlite 200 and, having been treated in accordance with Example 1, contains nickel, is heated in a stirred vessel to 140°–145° C., whilst stirring. After filtering off the exchanger whilst the reaction solution is hot, 280 parts of heptadecyl carbamate are obtained. This corresponds to a yield of 94% of theory. The product has a melting point of 53°–54° C.

EXAMPLE 11

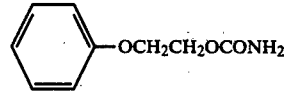

A mixture of 659 parts of phenylglycol, 180 parts of urea and 9 parts of a cation exchanger which is commercially available under the registered name Amberlyst 15 and, having been treated in accordance with Example (1a), contains nickel, is heated to 130° C. whilst stirring. The temperature is raised to 150° C. in the course of 6 hours and is then maintained thereat for a further 4 hours. After filtering off the exchanger whilst the reaction solution is hot, the filtrate is cooled to room temperature. After standing for several hours, the phenylglycol carbamate which has precipitated is filtered off. After evaporating off the excess phenylglycol under reduced pressure, a total of 499 parts of phenylglycol carbamate are obtained. This corresponds to a yield of 92% of theory. Melting point=105°–106° C.

EXAMPLE 12

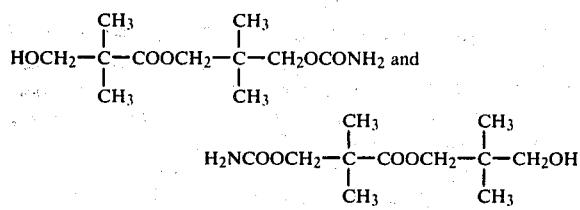

612 parts of neopentylglycol hydroxypivalate, 180 parts of urea and 9 parts of a cation exchanger which is commerically available under the registered name Amberlite 200 and, having been treated in accordance with Example (1a), contains nickel, are heated to 130° C. in a stirred apparatus, whilst a slight stream of nitrogen is passed through the mixture. The temperature is raised to 150° C. in the course of 10 hours. After filtering off the exchanger whilst the reaction solution is hot, 714 parts of 1:1 mixture of neopentylglycol hydroxypivalate carbamate isomers $n_D^{20} = 1.4613$ are obtained. This corresponds to a yield of 96% of theory.

EXAMPLE 13

810 parts of a polyether-diol having the structure H(OCH$_2$CH$_2$)$_{18}$OH, 60 parts of urea and 3.6 parts of a cation exchanger which is commercially available under the registered name Amberlite 200 and, having been treated in accordance with Example (1a), contains nickel, are mixed, and heated to 130° C., in a stirred apparatus. The temperature is then raised to 150° C. in the course of 6 hours and kept thereat for a further 4 hours. The exchanger is filtered off whilst the reaction solution is hot. 805 parts of carbamate of the formula H—(OCH$_2$CH$_2$)$_{18}$OCONH$_2$, of melting point 32°-34° C., are obtained. This corresponds to a yield of 94% of theory. The product is colorless and pasty.

EXAMPLE 14

414 parts of polyether-diol having the structure H—(OCH$_2$CH$_2$)$_9$OH, 60 parts of urea and 4 parts of a cation exchanger which is commercially available under the registered name Amberlite 200 and, having been treated in accordance with Example (1a), contains nickel, are heated to 130° C. The temperature is raised to 150° C. in the course of 6 hours and is then maintained thereat for a further 4 hours. After filtering off the exchanger, 415 parts (91% of theory) of monocarbamate of the formula H—(OCH$_2$CH$_2$)$_9$OCONH$_2$ are obtained.

Refractive index $n_D^{20} = 1.4708$.

EXAMPLE 15 (USE)

595 parts of the methoxyethyl carbamate manufacture according to Example (1b), 750 parts of a 40 percent strength by weight formaldehyde solution and 6 parts of a 50 percent strength by weight sodium hydroxide solution are heated in a stirred apparatus for 3 hours at 50° C., whilst stirring. This solution is neutralized with dilute sulfuric acid and then made up to 1,790 parts with water. This then constitutes a 50 percent strength by weight solution of dimethylolmethoxyethyl carbamate.

A bleached and mercerized cotton fabric (poplin) weighing 125 g/square meter was impregnated, on a padder, with a solution prepared by diluting 150 parts of a 50 percent strength by weight aqueous solution of N,N-dimethylolmethoxyethyl carbamate, 1 part of a reaction product of 7 moles of ethylene oxide with 1 mole of isooctylphenol and 30 parts of magnesium chloride hexahydrate to 1,000 parts by volume with water. The impregnated fabric is squeezed off to a wet pick-up of from 70 to 75% and is dried to 6-8% residual moisture content on a tender frame at 110° C. The treated fabric is then heated for 4 minutes at 160° C. on a tender frame. The technological data are summarized in the Table which follows.

TABLE

| | Untreated fabric | Finished fabric |
|---|---|---|
| Dry crease angle according to DIN 53,890 (warp + filling) (°C.) | 122° | 253° |
| Dry crease angle after 3 machine washes, each of 120 minutes, at the boil (warp + filling) (°C.) | 121° | 248° |
| Wet crease angle according to DIN 53,891 (warp + filling) (°C.) | 129° | 252° |
| Wet crease angle according to DIN 53,891, after 3 machine washes, each of 120 minutes, at the boil (warp + filling) (°C.) | 128° | 248° |
| Wrinkle-resist test according to AATCC 886-1964-T | 1.5 | 4.5 |
| Tensile strength, 40 × 100 mm (DIN 53,857) finish, filling, in Kg | 40.0 | 27.5 |
| After 1 alternating chlorination treatment (AATCC 92-1971) Tensile strength, 40 × 100 mm, filling, in kg | 40.5 | 27.3 |
| After 3 alternating chlorination treatments (AATCC 92-1971) Tensile strength, 40 × 100 mm, filling, in kg | 40.0 | 27.0 |
| After 5 alternating chlorination treatments (AATCC 92-1971) Tensile strength, 40 × 100 mm, filling, in kg | 39.2 | 27.0 |

We claim:

1. A process for the manufacture of carbamates of the formula $$R^1 \!\!-\!\!(O\!-\!R^2)_{\overline{m}}\!-\!O\!-\!\overset{\overset{\displaystyle O}{\|}}{C}\!-\!NH_2 \qquad I$$

where R$^1$ is an aliphatic, cycloaliphatic or araliphatic radical which may be interrupted by one or more $$-\overset{\overset{\displaystyle O}{\|}}{C}\!-\!O\!- \text{ or } -\overset{\overset{\displaystyle O}{\|}}{C}\!-\!\overset{\overset{\displaystyle H}{|}}{N}\!- \text{groups}$$

and/or oxygen atoms, R$^2$ is an aliphatic radical of at least 2 carbon atoms which is optionally interrupted by one or more $$-\overset{\overset{\displaystyle O}{\|}}{C}\!-\!O\!- \text{ or } -\overset{\overset{\displaystyle O}{\|}}{C}\!-\!\overset{\overset{\displaystyle H}{|}}{N}\!- \text{groups}$$

and/or oxygen atoms, or is

where the individual $R^3$'s may be identical or different and each is a cycloaliphatic, araliphatic or aromatic radical, and n is an integer from 2 to 6, and m is 0 or a positive integer, or $R^1$ is phenyl, or if m is not less than 1, $R^1$ is hydrogen

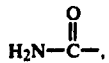

wherein alcohols of the formula $$R^1+O+R^2{}_mOH \qquad II$$

where $R^1$, $R^2$ and m have the above meanings except for R' being

are reacted with urea in the presence of cation exchangers containing nickel ions, said exchangers having been prepared by exchanging the nickel ions into the preformed cation exchangers, said cation exchangers being selected from the group consisting of phenolic resins, polystyrenesulfonic acid resins, bifunctional condensation resins, styrenephosphonic acid resins, styrenephosphinic acid resins, resorcinol resins or aliphatic or aromatic carboxylic acid resins.

2. A process as claimed in claim 1, wherein the reaction is carried out with from 0.5 to 1 mole of urea per mole of starting material II.

3. A process as claimed in claim 1, wherein the reaction is carried out with from 2 to 2.5 moles of urea per mole of starting material II.

4. A process as claimed in claim 1, wherein the reaction is carried out with from 2 to 2.2 moles of urea per mole of starting material II.

5. A process as claimed in claim 1, wherein the reaction is carried out at a temperature from 100° to 160° C.

6. A process as claimed in claim 1, wherein the reaction is carried out at a temperature from 125° to 150° C.

7. A process as claimed in claim 1, wherein the reaction is carried out in an organic solvent which is inert under the reaction conditions.

8. A process as claimed in claim 1, wherein the reaction is carried out with a charge of from 0.01 to 0.2 part by weight of nickel per part by weight of exchanger, and with from 0.01 to 0.25 part by weight of exchanger per part by weight of urea.

* * * * *

UNITED STATES PATENT AND TRADEMARK OFFICE
CERTIFICATE OF CORRECTION

PATENT NO. : 4,156,784
DATED : May 29, 1979
INVENTOR(S) : DOCKNER ET AL

It is certified that error appears in the above—identified patent and that said Letters Patent is hereby corrected as shown below:

IN THE CLAIMS:

Column 13, line 13, after "hydrogen" insert --or--

Column 13, the fifth formula should be corrected to read as follows:

-- $R^1\!-\!(O\text{-}R^2)_m OH$ --

Signed and Sealed this

Fifteenth Day of April 1980

[SEAL]

Attest:

SIDNEY A. DIAMOND

Attesting Officer      Commissioner of Patents and Trademarks